(12) United States Patent
Zombo

(10) Patent No.: US 9,670,793 B2
(45) Date of Patent: Jun. 6, 2017

(54) IR SENSOR/SYSTEM FOR DETECTION OF HEATING ASSOCIATED WITH CRACK PROPAGATION DURING OPERATION OF ROTATING EQUIPMENT

(71) Applicant: Siemens Energy, Inc., Orlando, FL (US)

(72) Inventor: Paul J. Zombo, Cocoa, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 455 days.

(21) Appl. No.: 14/255,991

(22) Filed: Apr. 18, 2014

(65) Prior Publication Data
US 2015/0300251 A1    Oct. 22, 2015

(51) Int. Cl.
| | | |
|---|---|---|
| F01D 17/08 | (2006.01) | |
| F01D 21/00 | (2006.01) | |
| G01N 25/72 | (2006.01) | |

(52) U.S. Cl.
CPC ......... F01D 17/085 (2013.01); F01D 21/003 (2013.01); G01N 25/72 (2013.01); F05D 2260/80 (2013.01); F05D 2260/83 (2013.01); F05D 2270/80 (2013.01)

(58) Field of Classification Search
CPC ...... F01D 5/005; F01D 17/085; F01D 21/003; F05D 2260/80; F05D 2260/83; F05D 2270/80; F02C 7/00; G01N 21/00; G01N 25/72; G01J 5/02; G02B 23/24; G02B 23/2446; G02B 23/2461; G06T 7/00; G06T 7/004; H04N 5/23293; H04N 5/23296; H04N 5/2252; H04N 5/2254; H04N 5/2256; H04N 5/232; H04N 5/23212; H04N 5/23238
USPC ........................ 60/39.02, 39.091, 39.33, 803; 250/227.14, 341.6; 348/46; 415/118
See application file for complete search history.

(56) References Cited

U.S. PATENT DOCUMENTS

| | | | | |
|---|---|---|---|---|
| 6,730,912 B2* | 5/2004 | Sun | ........................ | G01N 25/72 250/341.6 |
| 7,064,330 B2* | 6/2006 | Raulerson | ............... | G01N 21/70 250/341.6 |
| 7,486,864 B2* | 2/2009 | Diatzikis | ............... | F01D 21/003 385/123 |
| 8,576,392 B2* | 11/2013 | Johnston | ................. | F01D 17/02 356/237.1 |
| 8,790,074 B2* | 7/2014 | Johnston | ............... | F01D 21/003 415/118 |
| 9,207,128 B2* | 12/2015 | McCarthy | ................ | G01K 1/14 |
| 9,267,378 B2* | 2/2016 | Delvaux | ............... | F01D 21/003 |
| 9,354,190 B2* | 5/2016 | Quinn | .................... | G01N 25/72 |

(Continued)

*Primary Examiner* — Bryon Gehman

(57) ABSTRACT

A thermal imaging system that detects the growth of cracks in a structural element, where the system has particular application for detecting the growth of cracks and similar defects in a turbine blade. The thermal imaging system includes at least one infrared (IR) fiber optic cable where a sensing end of the fiber optic cable is positioned in close proximity to a location where a crack in the structural element may occur. Infrared emissions generated as a result of crack growth are collected by the IR fiber cable and transmitted by the cable to an infrared monitoring device. The amount of heat that is detected provides an indication of whether the crack is growing, and if so, at what rate.

15 Claims, 2 Drawing Sheets

(56) References Cited

U.S. PATENT DOCUMENTS

| | | | |
|---|---|---|---|
| 2005/0198967 A1* | 9/2005 | Subramanian | C23C 4/18 |
| | | | 60/803 |
| 2011/0267428 A1* | 11/2011 | George | G01N 21/9515 |
| | | | 348/46 |
| 2012/0194667 A1* | 8/2012 | Banerjee | G01J 5/0088 |
| | | | 348/135 |
| 2014/0168433 A1* | 6/2014 | Frank | H04N 5/33 |
| | | | 348/143 |
| 2015/0219575 A1* | 8/2015 | Pettit | G01N 25/72 |
| | | | 374/47 |

* cited by examiner

IR SENSOR/SYSTEM FOR DETECTION OF HEATING ASSOCIATED WITH CRACK PROPAGATION DURING OPERATION OF ROTATING EQUIPMENT

BACKGROUND OF THE INVENTION

Field of the Invention

This invention relates generally to a system and method for detecting cracks or similar defects in a structural element and, more particularly, to a thermal imaging system that detects the propagation or growth of a crack in a structural element by collecting infrared emissions using a fiber optic cable that occur as a result of the crack generating heat as it expands.

Discussion of the Related Art

Many devices and machines have moveable parts and components that may operate in a manner that could cause undesirable wear and metal fatigue. For example, turbines, compressors and other similar machines have rotating shafts including blades, vanes and other elements disposed thereon. Operation of such machines may cause unwanted contact of the blades and other moving components with housings and other structures within the machine. This unwanted contact could be caused by many factors, such as thermal expansion, high shaft rotation speed, motor surge, etc.

One particular area of concern is the formation of cracks that may occur in turbine blades as a result of metal fatigue and stress through continuous use. Particularly, high speed rotating blades in a steam or gas turbine may cause high cycle fatigue in the blades, which could create cracks in the blade and associated blade structures, especially where the blade attaches and is mounted to a central disk. Those cracks could rapidly grow and expand undetected at any particular point in time, possibly causing catastrophic failure of the turbine. For example, certain operational parameters of a turbine, such as rotation speed, temperature, pressure, load, etc., may create variations in component fatigue possibly resulting in crack formation, where it may be desirable to identify those operating parameters so as to avoid them.

A number of technologies have been employed in the art to detect cracks and other defects in structural elements such as turbine blades. For example, it is known to heat a structural element using an external heat source that causes emissions in the infrared wavelengths from the structural element. Immediate areas around defects in the structural element generally have a different cooling rate than the non-damaged portion of the element. Also, because a crack looks like a knife edge to the planar heat pulse, and therefore no, or minimal, heat reflections occur from the crack making it difficult or impossible to see in a thermal image. A thermal or infrared imaging camera can be used to detect the infrared emissions to identify areas in the structural element having a lower temperature.

It is also known in the art to ultrasonically excite a structural element that causes edges of cracks to rub against each other and generate heat, which can be detected by a thermal imaging camera. Particularly, an acoustic thermal effect occurs when sound waves propagate through a solid body that contains a crack or other defect causing it to vibrate. Because the faces of the crack ordinarily do not vibrate in unison as the sound waves pass, dissipative phenomena, such as friction between the faces, will convert some of the vibrational energy to heat.

Another known crack detection technique employs an electromagnetic coil that induces eddy currents in the structural element that changes its pattern at a crack or other defect, which then can be detected. The coil is moved around on the structural element, and the eddy current pattern changes at a crack or other defect. The complex impedance in the coil changes as the eddy current changes, which can be observed on an oscilloscope.

It also has been proposed in the art to employ fiber Bragg grating (FBG) sensors that are formed in a fiber and reflect a narrow wavelength of an optical input beam. By positioning the FBG sensor at a location distal from the beam input, damage to the fiber between the sensor and the input will prevent the reflected wavelength from being received, possibly indicating a defect in the structure.

One technique for detecting cracks in turbine blades is to obtain blade vibration measurements and identify changes in blade vibrations, which indicates the presence of a crack. This process has proven to be successful for detecting cracks in turbine blades for millimeter size defects. However, this technique is not able to identify when the crack is actively growing.

Currently, no suitable technology is available that is able to detect the propagation or growth of a crack, and especially the growth of a crack in a turbine blade.

SUMMARY OF THE INVENTION

In accordance with the teachings of the present invention, a thermal imaging system is disclosed that detects the growth of cracks in a structural element, where the system has particular application for detecting the growth of cracks and similar defects in a turbine blade. The thermal imaging system includes at least one infrared (IR) fiber optic cable where a sensing end of the fiber optic cable is positioned in close proximity to a location where a crack in the structural element may occur. Infrared emissions generated as a result of crack growth are collected by the IR fiber cable and transmitted by the cable to an infrared monitoring device. The amount of heat that is detected provides an indication of whether the crack is growing, and if so, at what rate.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a thermal imaging system for monitoring crack propagation and growth in a structural element is merely exemplary in nature and is in no way intended to limit the invention or its applications or uses. For example, the thermal imaging system has particular application for detecting crack growth occurring in turbine blades. However, as will be appreciated by those skilled in the art, the thermal imaging system may have application for detecting cracks in other structures.

As will be discussed in detail below, the present invention proposes a thermal imaging system that is operable to collect infrared emissions from a crack in a structural element as the crack is growing. A crack or other similar defect that has formed in a particular structural element, such as a turbine blade, will typically be at the same temperature as the surrounding material of the structural element. However, when that crack or similar defect increases in size or grows, such as a crack extending in length, that growth process generates localized heating causing the tip of the crack to be at a slightly higher temperature than the surrounding material. This crack formation activity can occur without actual measurable crack growth, such as when crack surfaces touch and rub against each other as a component is loaded, which may cause frictional or thermo-elastic heating or cooling. Further, a crack could cause a step surface offset associated with a heat transfer difference from side-to-side of the crack. By providing an IR fiber optic cable, or other IR detecting device, positioned proximate to the location where the crack is forming, IR emissions from the increase in temperature at the tip of the crack can be collected by the fiber optic cable, transmitted along the fiber cable, and be detected by a monitoring device. The amount of heat that is generated is proportional to the size of the crack and the speed that the crack is forming and expanding.

The monitoring device can be calibrated to identify the size of the crack and its rate of formation. Further, as the crack periodically grows over time, that growth can be charted or graphed to give an indication of when the size of the crack will require that the machine, such as a turbine, be shut down for maintenance before a catastrophic failure occurs. Also, by monitoring the turbine operating parameters, such as temperature, rotation speed, pressure, load, etc., and comparing those parameters to the times that crack growth is occurring, the parameters that cause crack growth can be avoided to the extent possible to prevent further crack expansion. Because turbine blades rotate during operation of the turbine, the collecting end of the fiber optic cable can be positioned at a proper location where all of the blades pass by the cable. Thus, a single fiber cable can be used to monitor all of the blades in a self-scanning operation.

Figure 1:
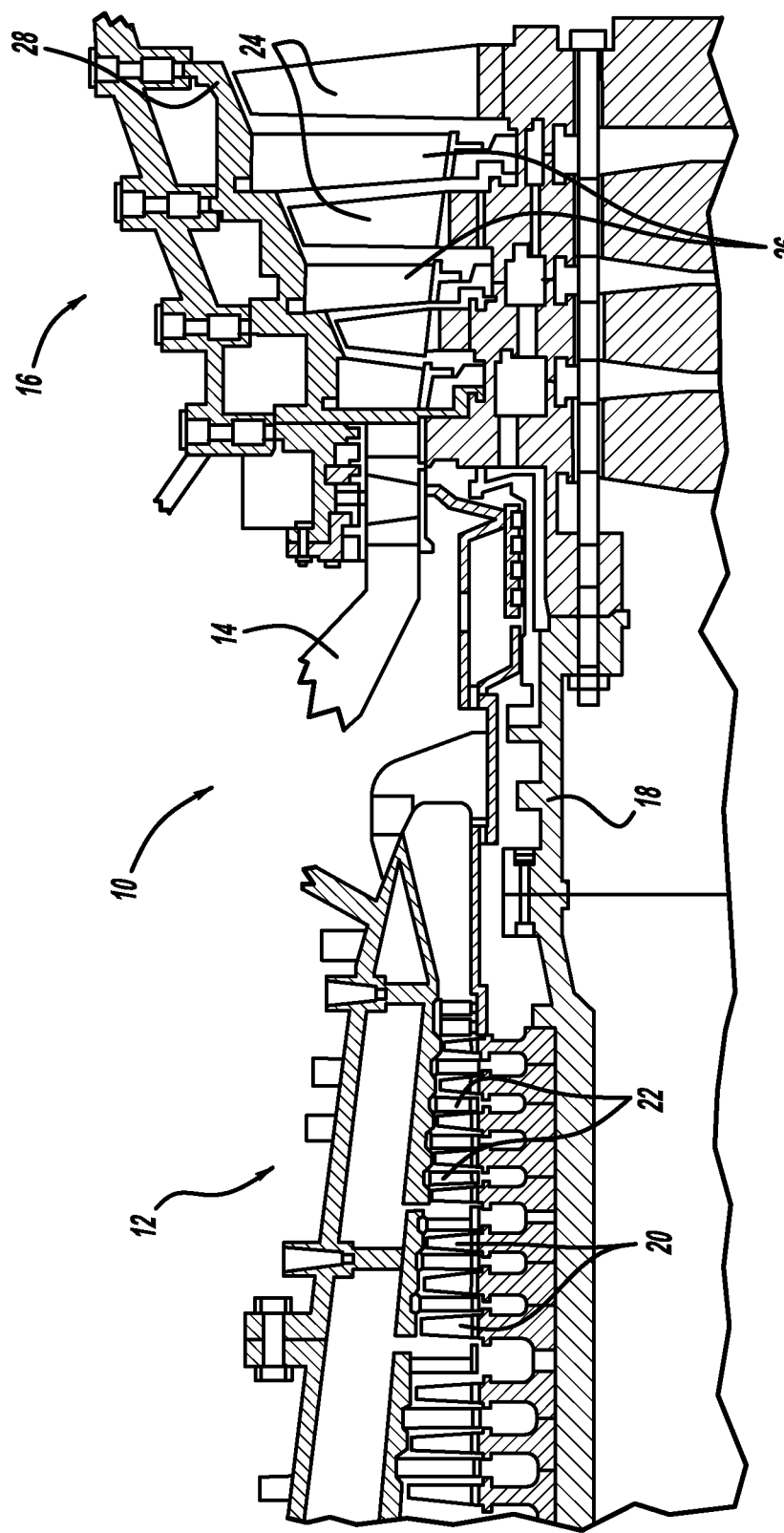
FIG. 1 is a cut-away, cross-sectional view of a gas turbine engine.

FIG. 1 is a cut-away, cross-sectional view of a portion of a gas turbine engine 10 including a compressor section 12, a combustion section 14 and a turbine section 16, where operation of the engine 10 rotates a shaft 18. Although FIG. 1 is specific to a gas turbine engine, it is intended to be a general representation of many types of turbines, such as steam turbines, including an L-0 steam turbine, that would benefit from the thermal imaging and detection system as discussed herein. As is well understood by those skilled in the art, gas turbine engines of this type have various applications, such as electric generators in a power generating plant, aircraft engines, ship engines, etc.

The compressor section 12 includes a plurality of rotatable blades 20 positioned between respective stationary vanes 22. Likewise, the turbine section 16 includes a plurality of rotatable blades 24 and stationary vanes 26 positioned therebetween. The vanes 26 are mounted to an appropriate structure within the turbine section 16 by a suitable support component 28, for example, a blade ring, as would be well understood by those skilled in the art. The blades 24 and the vanes 26 are designed for high temperature applications, and typically are made from a suitable super-alloy material, for example, a nickel, cobalt or iron based super-alloy material, which may be coated with a thermal barrier coating (TBC), for example, yttria-stabilized zirconia. The combustion section 14 includes a plurality of combustors circumferentially positioned around the turbine engine 10.

Air is drawn into the compressor section 12 where it is compressed and driven towards the combustion section 14. The combustion section 14 mixes the air with a fuel where it is ignited to generate a working gas typically having a temperature above 1300° C. The working gas expands through the turbine section 16 and is guided across the blades 24 by the vanes 26. As the working gas passes through the turbine section 16, it causes the blades 24 to rotate, which in turn causes the shaft 18 to rotate, thereby providing mechanical work. A more detailed discussion of a gas turbine engine of this type can be found in U.S. Pat. No. 7,582,359, titled Apparatus and Method of Monitoring Operating Parameters of a Gas Turbine, assigned to the assignee of this application and herein incorporate by reference.

Because of the harsh environment within the gas turbine engine 10, many of the components in the engine 10, such as the blades 20 and 24 and the vanes 22 and 26, may be subjected to undesirable wear and cycling fatigue. As discussed above, it may be desirable to monitor these components to detect this wear and the growth of cracks forming therein.

Figures 2, 3:
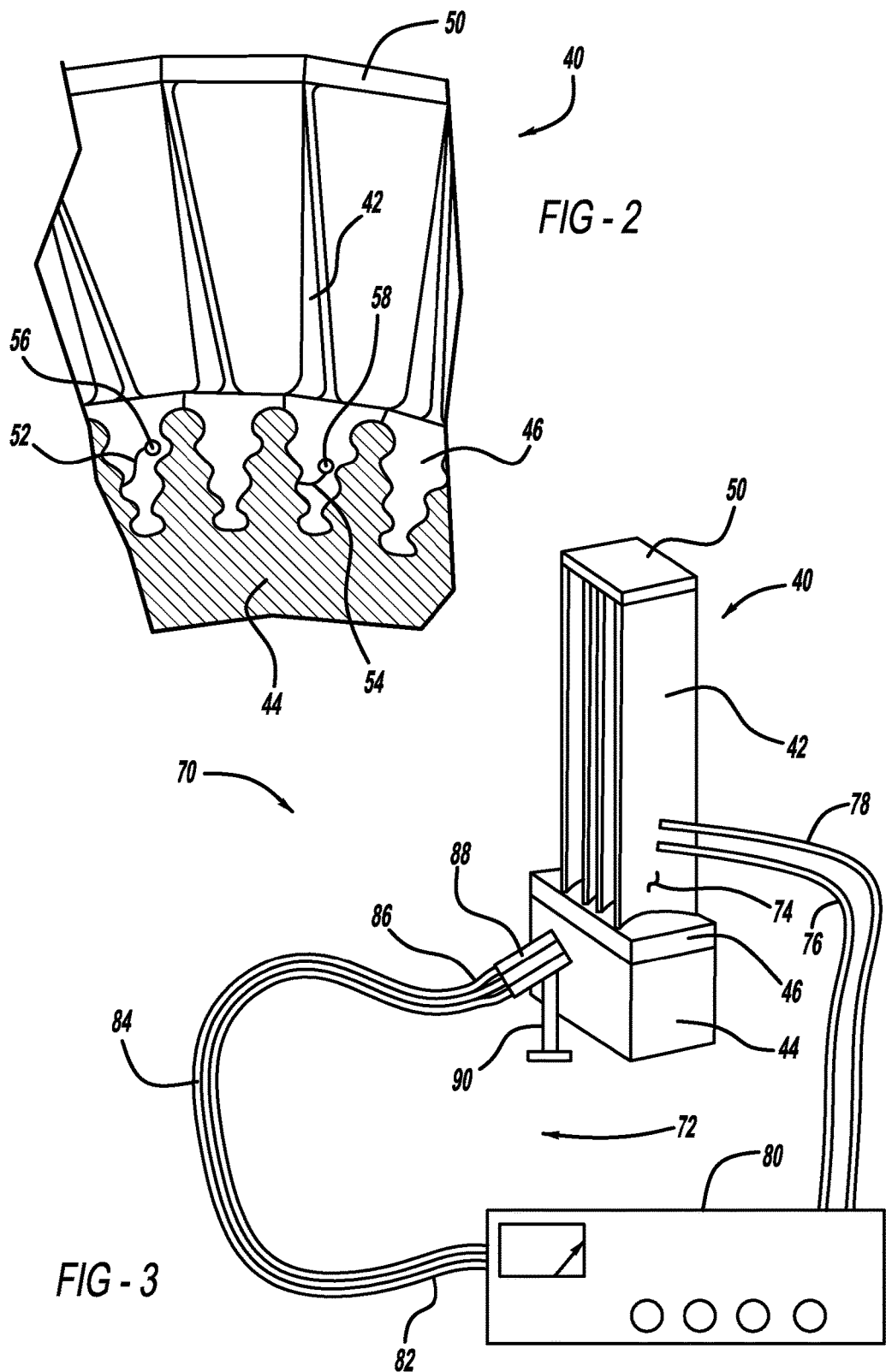
FIG. 2 is a cut-away, cross-sectional view showing a group of turbine blades.
FIG. 3 is an illustration of an infrared thermal monitoring system positioned proximate to the group of turbine blades.

FIG. 2 is a cut-away, cross-sectional view of a group 40 of turbine blades 42 showing where crack formation may occur or is likely to occur. The group 40 is a portion of a complete circumference of the turbine blades for a turbine. The turbine blades 42 are mounted to a central disk 44 by mounting structures 46 where the central disk 44 is mounted to a shaft (not shown). A blade ring 50 is mounted to a distal end of the blades 42. Because of wear and cycling fatigue during operation of the turbine, cracks are susceptible to be formed in the blades 42 and/or the mounting structures 46. To illustrate this, a small crack 52 and a large crack 54 are shown in two of the structures 46.

The occurrence or formation of the cracks 52 and 54 may not immediately present a problem for turbine failure, but the cracks 52 and 54 are likely to grow, and possibly grow very quickly, which could eventually present a turbine failure issue and possibly a catastrophic turbine failure. As mentioned above, when the cracks 52 and 54 grow a small amount of localized heat is generated at the crack tip, which gives off IR emissions. This localized heating is represented as hot tip 56 at the end of the crack 52 and hot tip 58 at the end of the crack 54. Although only a small amount of heat is given off during crack formation, possibly only on the order of 0.01 C.°, this heat can be thermally detected by modern fiber optic cables and other IR sensing equipment, such as an infrared camera, even in the high temperature environment of a gas or steam turbine.

FIG. 3 is an illustration 70 showing the group 40 of the turbine blades 42 and a thermal imaging system 72 of the type being described herein. The thermal imaging system 72 is intended to represent any configuration of one or more IR detectors suitable for the purposes discussed herein. For example, the thermal imaging system can include a single fiber optical cable, a linear array of fiber optic cables aligned in a straight line, a select array of fiber optic cables, where a group of fiber optic cables are aimed along the path of crack propagation, a select array of fiber optic cables, where the fiber optic cables are aimed at suspect crack locations, a planar array of individual fiber optic cables, and an infrared camera. For one embodiment, the illustration 70 shows a crack 74 forming in one of the blades 42. A plurality of fiber optic cables 76 and 78 are strategically positioned and adhered to the blade 42 at different locations so that as the crack 74 grows, the cables 76 and 78 will detect IR heat emissions from that growth. The fiber optic cables 76 and 78 can be any fiber cable suitable to collect and transmit IR radiation. As the growth of the crack 74 approaches a particular one of the cables 76 and 78 and crosses their path, a progressive alarm can be given identifying the length of the crack 74.

In one specific non-limiting example, the thermal imaging system 72 includes an infrared monitoring device 80 having a number of channels where a detecting end 82 of each of a plurality of infrared fiber optic cables 84 is connected to a separate channel. The fiber optic cables 84 can be any fiber cable suitable to collect and transmit IR radiation. Typically, the fiber cable 84 will include an inner fiber core surrounded by an outer cladding layer having a higher index of refraction than the core to contain the optical signal propagation within the fiber core, and an outer protective layer. The fiber core may have a diameter of about 10 μm, which provides a multi-mode fiber for propagating multiple optical modes. A collecting end 86 of each fiber optic cable 84 includes an end cap 88 and is positioned proximate to a proximal end of the blades 42 at the mounting structures 46. The collecting ends 86 are positioned a suitable distance from the blades 42 to collect IR emissions from the cracks 52 and 54 as they grow. It is noted that the end caps 88 are merely provided to protect the ends of the fiber cables 84 and are not necessary for the cables 84 to collect the IR emissions. Any suitable optical element, such as a lens, can be provided in combination with the collecting ends 86 to enhance collection of the IR emissions.

A securing device 90 is provided to hold the cables 84 at the proper location and can be attached to any suitable structure (not shown) within the turbine. As long as there is enough room to position and thread the cables 84 through the turbine, the system 72 is able to detect IR emissions. As the blades 42 rotate they all pass by the collecting ends 86 of the cables 84 in a self-scanning operation. A plurality of the fiber cables 84 is provided in an aligned configuration along a row to best be able to collect IR emissions as the crack expands and lengthens. In this non-limiting embodiment, the system 72 includes three separate infrared fiber optic cables although any suitable number can be provided, including a single cable.

The monitoring device 80 can provide any of a number of operations in addition to identifying an increase in temperature from the collected IR radiation. For example, the device 80 can analyze that temperature and use a look-up table to identify the type of crack, the size of the crack, the rate that the crack is growing, etc. The device 80 can store this information for historical purposes or otherwise and can provide charts and graphs identifying crack growth over time. The device 80 can also monitor operating conditions of the turbine, such as temperature, rotation speed, pressure, load, etc., and compare those conditions to the times that crack growth is occurring, so that the conditions that cause crack growth can be avoided to the extent possible to prevent further crack expansion. The device 80 can provide alarms or other warnings, or even shut the turbine down if crack growth warrants such an action.

The foregoing discussion discloses and describes merely exemplary embodiments of the present invention. One skilled in the art will readily recognize from such discussion, and from the accompanying drawings and claims, that various changes, modifications and variations can be made therein without departing from the scope of the invention as defined in the following claims.

What is claimed is:

1. A thermal imaging system for detecting crack growth in a structure, said system comprising:
    at least one infrared (IR) fiber optic cable including a collection end and a detection end, the fiber optic cable configured to collect and transmit infrared radiation; and
    a detection and monitoring device coupled to the detection end of the at least one IR fiber optic cable, the at least one infrared fiber optic cable being operable to collect IR emissions generated by heat from the growth of the crack in the structure at the collection end and said detection and monitoring device being operable to receive the IR emissions at the detection end and convert the IR emissions to a signal that identifies the crack growth.

2. The system according to claim 1 wherein the structure is a turbine blade.

3. The system according to claim 1 wherein the at least one IR fiber optic cable includes one or more of the group consisting of a single fiber optical cable, a linear array of fiber optic cables aligned in a straight line, a select array of fiber optic cables, where a group of the fiber optic cables are aimed along a path of crack propagation, a select array of fiber optic cables, where the fiber optic cables are aimed at suspect crack locations, a planar array of individual fiber optic cables, and an infrared camera.

4. The system according to claim 1 wherein the at least one fiber optic cable is a plurality of IR fiber optic cables each including a collection end and a detection end.

5. The system according to claim 4 wherein the collection ends of all of the fiber optic cables are aligned in a row.

6. The system according to claim 4 wherein the detection end of each fiber optic cable is coupled to the detection and monitoring device.

7. The system according to claim 1 wherein the detection and monitoring device monitors operating parameters of a machine in which the structure is located and identifies the operating parameters that cause crack growth to occur.

8. The system according to claim 1 wherein the detection and monitoring device determines the size of the crack and rate that crack growth is occurring.

9. A gas turbine comprising:
    a shaft rotatably provided along a center line of the turbine;
    a compressor section responsive to a working fluid and being operable to compress the working fluid to produce a compressed working fluid;
    a combustion section in fluid communication with the compressor section that receives the compressed working fluid, said combustion section mixing the compressed working fluid with a fuel and combusting the compressed fluid and fuel mixture to produce a hot working fluid;
    a turbine section in fluid communication with the combustion section, said turbine section expanding the hot working fluid to produce mechanical power through rotation of the shaft; and
    a thermal imaging system for detecting crack growth on a structure in the compressor section, the combustion section or the turbine section, said system including at least one infrared (IR) fiber optic cable including a collection end and a detection end, and a detection and monitoring device coupled to the detection end of the at least one IR fiber optic cable, the infrared fiber optic cable being operable to collect IR emissions generated by heat from the growth of the crack in the structure at the collection end and said detection and monitoring device being operable to receive the IR emissions at the detection end and convert the IR emissions to a signal that identifies the crack growth.

10. The turbine according to claim 9 wherein the structure is a turbine blade.

11. The turbine according to claim 9 wherein the at least one fiber optic cable is a plurality of IR fiber optic cables each including a collection end and a detection end.

12. The turbine according to claim 11 wherein the collection ends of all of the fiber optic cables are aligned in a row.

13. The turbine according to claim 11 wherein the detection end of each fiber optic cable is coupled to the detection and monitoring device.

14. The turbine according to claim 9 wherein the detection and monitoring device monitors operating parameters of a machine in which the structure is located and identifies the operating parameters that cause crack growth to occur.

15. The turbine according to claim 9 wherein the detection and monitoring device determines the size of the crack and rate that crack growth is occurring.

\* \* \* \* \*